US00PP11102P

United States Patent [19]

Fear et al.

[11] Patent Number: Plant 11,102

[45] Date of Patent: Oct. 19, 1999

[54] RASPBERRY PLANT NAMED 'ANNAMARIA'

[75] Inventors: Carlos D. Fear, Aptos, Calif.; Mella-Dee M. Mayberry, Georgetown, Del.

[73] Assignee: Sweetbriar Development, Inc., Watsonville, Calif.

[21] Appl. No.: 09/019,173

[22] Filed: Feb. 5, 1998

[51] Int. Cl.[6] ..... A01H 5/00

[52] U.S. Cl. ..... Plt./204

[58] Field of Search ..... Plt./204

[56] References Cited

U.S. PATENT DOCUMENTS

P.P. 6,493 12/1988 Wilhelm ..... Plt./204
P.P. 7,437 2/1991 Ackerman ..... Plt./204

*Primary Examiner*—Howard J. Locker
*Assistant Examiner*—Wendy A. Baker
*Attorney, Agent, or Firm*—Pennie & Edmonds LLP

[57] ABSTRACT

The present invention relates to a new and distinct cultivar of red raspberry plant named 'AnnaMaria', botanically identified as *Rubus idaeus* L. The new cultivar is distinguished from other red fruited cultivars by its large fruit of excellent firmness, its high yielding capacity on both primocane and floricane crops, and light red color of the fruit.

2 Drawing Sheets

BACKGROUND OF THE INVENTION

The new cultivar was developed from the hybridization of the selection 'E39-3' (unpatented variety) as the seed parent with the selection 'F164-3' (an unpatented variety) as the pollen parent. The parents were crossed in the Fall of 1992, whereafter fruit and seed were collected to produce seedlings for field planting in Watsonville, Calif. in 1992. The new cultivar was selected from these seedlings in August 1993 for its large fruit size, high productivity, and fruit flavor. The new cultivar has been grown and asexually propagated by in vitro shoot tip culture, root sucker division and root cuttings at the Cassin Ranch in Santa Cruz county, California, and has been shown to maintain the desired and distinguishing characteristics after propagation over several generations.

SUMMARY OF THE INVENTION

This invention provides a new and distinct cultivar of red raspberry plant named 'AnnaMaria'. The new cultivar is botanically identified as *Rubus idaeus* L. The 'AnnaMaria' cultivar produces a primocane crop which begins in mid July to early August and continues through November. The floricane crop begins in late April and continues through late June. Both the primocane and floricane yields are very high relative to other comparable cultivars. The fruit of 'AnnaMaria' is large and firm and remains consistently so throughout its harvest period. The fruit of 'AnnaMaria' is light red.

BRIEF DESCRIPTION OF THE DRAWINGS

The accompanying photographs show typical specimens of the primocane fruit, leaves and shoot of the new cultivar, in color as nearly true as it is reasonably possible to make in color illustrations of these characteristics.

DETAILED BOTANICAL DESCRIPTION

Figure 1:
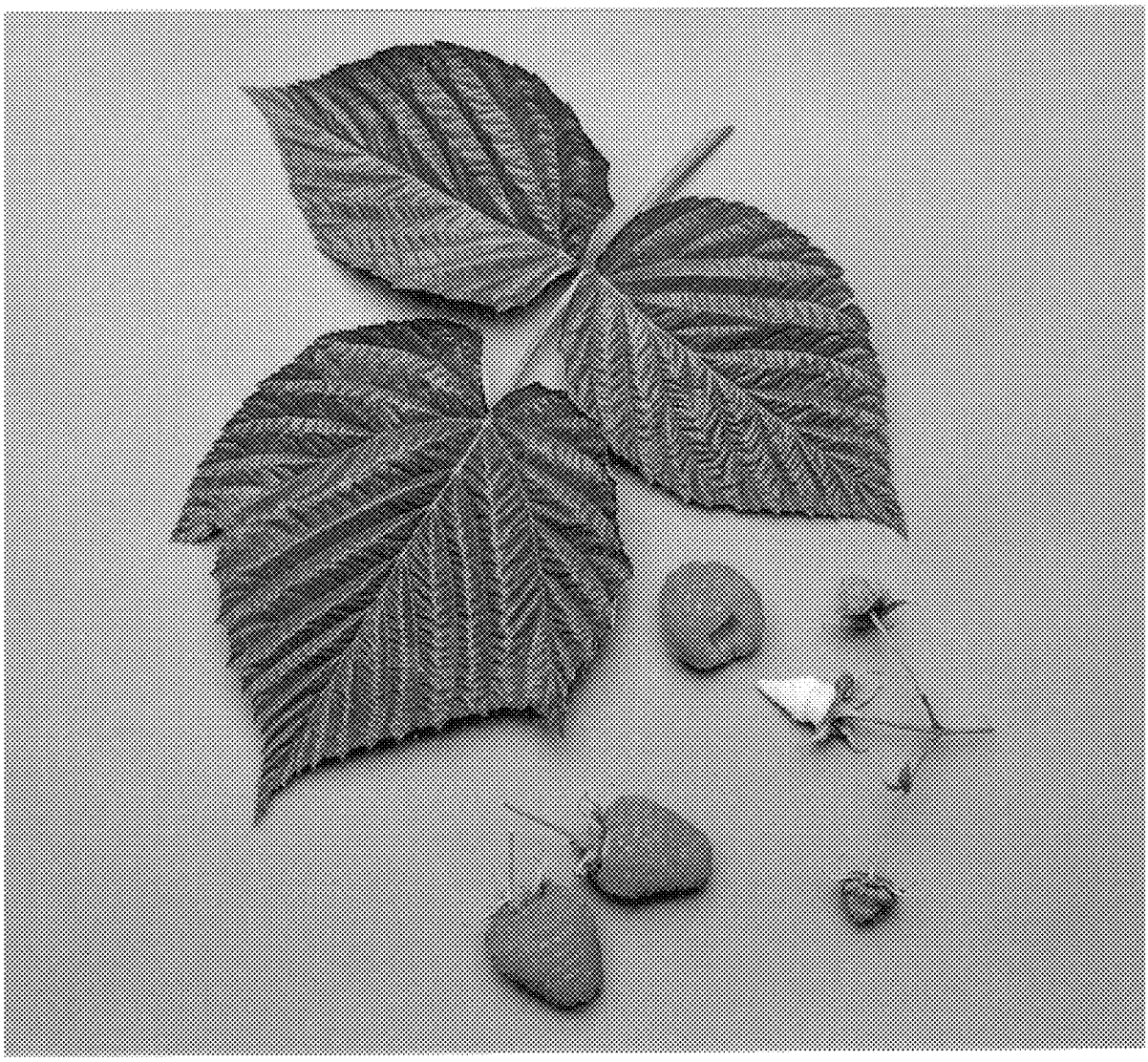
FIG. 1 is a photograph of a primocane mature leaf and fruit.
Figure 2:
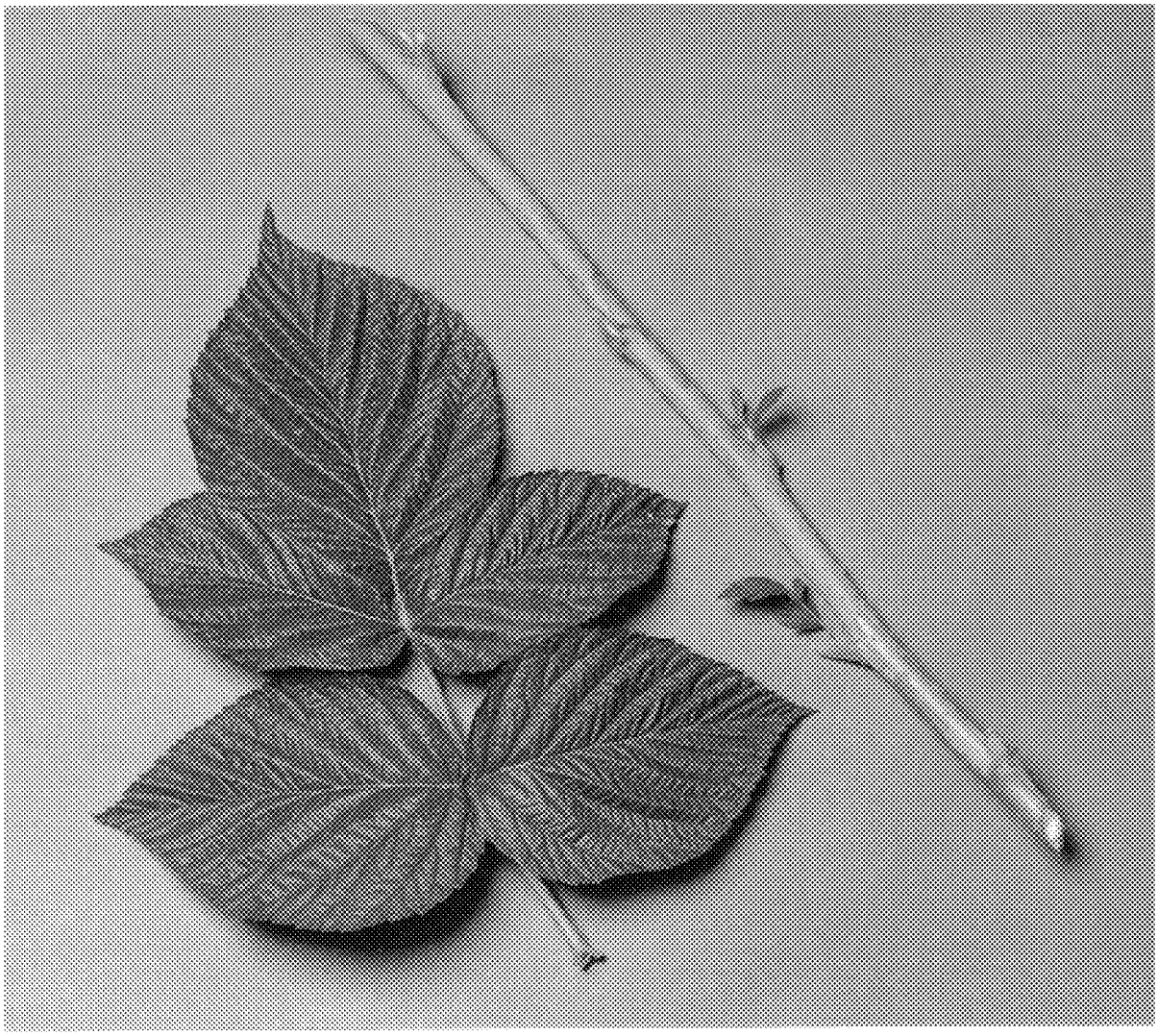
FIG. 2 is a photograph of a primocane shoot and leaf.

The following detailed description of the new raspberry cultivar, 'AnnMaria', is based upon observations taken of plants and fruit grown in Watsonville, Calif. between 1994 and 1997, and is believed to apply to plants of the 'AnnaMaria' cultivar grown in similar conditions of soil and climate elsewhere.

Throughout the specification, color names beginning with a small letter signify that the name of the color, as used in common speech, is aptly descriptive. Color names beginning with a capital letter and followers by an alphanumeric code designating the color according to The R.H.S. Colour Chart published by The Royal Horticultural Society of London, England. Color designations, descriptions, and other phenotypical descriptions may deviate from the stated values and descriptions depending upon variation in environmental, seasonal, climatic and cultural conditions.

Tables 1 and 2 present information on the plant and fruit characteristics of the new cultivar 'AnnaMaria' compared with characteristics of the unpatented raspberry cultivars 'Heritage', 'Summit' and 'Amity'. The closest cultivars to 'AnnaMaria' are 'Amity' for its cropping cycle and 'Summit' for its primocare production. Observations of the cultivars were taken under similar conditions.

The new variety is particularly characterized and distinguished from other cultivars listed in tables 1 and 2 by its high yielding capacity on both primocane and floricane crops, and large fruit size, firmness of the fruit and fruit flavor.

The fruit color of 'AnnaMaria' is light red at harvest with little color change after harvest. Fruit of 'AnnaMaria' is large, separates very easily from the receptacle and is of very good firmness at harvest.

'AnnaMaria' is distinguished from its pollen parent, 'F164-3', as having a higher yield and greater fruit firmness. 'AnnaMaria' is distinguished from its seed parent, 'E39-3', by having a higher yield and fruit that is less firm.

ISOZYME CHARACTERISTICS

In addition to the morphological description above, the new variety 'AnnaMaria' has been analyzed to obtain an indication of its genetic makeup to provide further means to identify the new variety and distinguishing it from some other somewhat similar and/or related raspberry varieties. Specifically, leaf samples of 'AnnaMaria' and the unpatented varieties 'Heritage' and 'Summit' were analyzed by electrophoresis for the isosozyme patterns of the enzymes phosphoglucoisomerase (PGI), malate dehydrogenase (MDH) and phosphoglucomutase (PGM) using the procedure described by J.C. Cousineau and D.J. Donnelly, "Use of isoenzyme analysis to characterize raspberry cultivars and detect cultivar mislabeling", *Hort Science* 27:1023–1025 (1992). The results of the electrophoresis analysis are presented in Table 3 with the letters representing the cultivar banding pattern for each enzyme as designated in the above-identified article.

DISEASE AND STRESS RESISTANCE

The cultivar is moderately susceptible to late leaf rust. Resistance is unknown to powdery mildew and root rots. Cold tolerance of the new cultivar has not been established. Post harvest fruit rot resistance is average in comparisons over many selections and varieties.

TABLE 1

PLANT CHARACTERISTICS OF 'ANNAMARIA'

| | Anna-Maria | Heritage | Summit | Amity |
|---|---|---|---|---|
| General | | | | |
| Plant size | large | large | small-medium | medium |
| Growth habit | erect | erect | semi-erect | erect |
| Productivity | very high | medium | high | low-medium |
| Self-fruitfulness | self-fruitful | self-fruitful | self-fruitful | self-fruitful |
| Primocane fruiting | | | | |
| percent of cane flowering as primocane | ~40–60 | ~5–20 | ~40–50 | ~20–35 |
| percent of total yield | ~50–70 | ~40–60 | ~50–70 | ~40–50 |
| Number of young shoots | few | medium | few | many |
| Primocanes | | | | |
| number fruiting laterals/cane | 11–23 (mean 17) | 2–14 (mean 8) | 9–15 (mean 12) | 6–14 (mean 10) |
| number of canes/crown | 2–6 (mean 4) | 3–5 (mean 4) | 2–7 (mean 3) | 1–6 (mean 3) |
| young shoot pigmentation | medium intensity red | medium intensity red | medium intensity red | medium intensity red |
| length (cm) | 175–225 (mean 198) | 182–230 (mean 208) | 137–212 (mean 164) | 135–208 (mean 168) |
| diameter (end of 1st year) | | | | |
| cane base (cm) | 0.8–1.7 (mean 1.2) | 0.9–1.4 (mean 1.2) | 0.8–1.3 (mean 1.1) | 0.8–1.5 (mean 1.1) |
| central ⅓ of cane (cm) | 0.7–1.2 (mean 0.9) | 0.8–1.1 (mean 1.0) | 0.7–1.0 (mean 0.8) | 0.6–1.0 (mean 0.8) |
| time of shoot emergence | late | very late | late | medium |
| prickles | | | | |
| pigmentation | green-brownish green | green-brownish green | brownish-purple-purple | purple |

TABLE 1-continued

PLANT CHARACTERISTICS OF 'ANNAMARIA'

| | Anna-Maria | Heritage | Summit | Amity |
|---|---|---|---|---|
| density on young shoots | medium | dense | sparse | sparse |
| attitude of tip | horizontal | downward | downward | horizontal |
| size | small | medium | medium | small |
| texture | heavy-rigid | rigid | heavy | heavy |
| presence and distribution on petioles | regularly distributed | regularly distributed | regularly distributed | regularly distributed |
| pubescence on canes | strong | absent or very weak | medium | medium |
| internodal distance (cm) | | | | |
| (at central ⅓ of cane) | 4.2–6.5 (mean 5.1) | 3.0–6.0 (mean 4.7) | 3.2–7.5 (mean 4.8) | 3.0–6.5 (mean 5.0) |
| lenticels | not visible | not visible | not visible | not visible |
| Floricanes | | | | |
| number nodes/lateral branch | 9–11 | 10–14 | 10–15 | 12–19 |
| number of flowers/node | 1–2 | 1–4 | 2–6 | 1–2 |
| Leaves | | | | |
| Arrangement | compound | compound | compound | compound |
| Relief between veins | medium | very weak | medium | medium |
| Cross section | flat-convex | concave | flat | concave-flat |
| Leaflet number | 3–5 | 3–5 | usually 5 | usually 3 |
| Terminal leaflet | | | | |
| length (cm) | 14.0 | 14.6 | 12.4 | 13.7 |
| width (cm) | 14.0 | 7.8 | 7.2 | 12.1 |
| shape | lobed | ovate | ovate | lobed |
| tip | acuminate | acuminate | acuminate | acuminate |
| base | cordate | acute | rounded | cordate |
| margin | doubly serrate | doubly serrate | doubly serrate | doubly serrate |
| Lateral leaflets (basal pair) | | | | |
| overlap | overlapping | free | overlapping | overlapping |
| orientation | opposite | opposite | opposite | opposite |
| shape | ovate | oblique | ovate-lobed | ovate-lobed |
| tip | acuminate | acuminate | acuminate | acuminate |
| base | weakly cordate-round | oblique | oblique-rounded | oblique |
| margin | doubly serrate | doubly serrate | doubly serrate | doubly serrate |
| length (cm) | 11.0 | 14.7 | 11.6 | 11.7 |
| width (cm) | 7.5 | 8.6 | 7.7 | 8.2 |
| Rachis length between terminal leaflet and adjacent lateral leaflets (cm) | 3.0–4.9 (mean 4.3) | 0.8–2.2 (mean 1.5) | 0.5–1.8 (mean 1.2) | 2.4–3.9 (mean 3.0) |

TABLE 1-continued

PLANT CHARACTERISTICS OF 'ANNAMARIA'

| | Anna-Maria | Heri-tage | Summit | Amity |
|---|---|---|---|---|
| Glossiness | medium | medium | medium | dull |
| Color | | | | |
| face | medium 147A | medium 137A, 139A | medium 137A | medium 147A |
| underside | 148C | 148C, 191B | 191B | 191A |
| Petiole | | | | |
| length (cm) | 6.3–10.7 (mean 8.3) | 6.6–8.5 (mean 7.6) | 5.8–8.9 (mean 7.4) | 4.0–8.2 (mean 6.0) |
| pigmentation of upper surface | weak | lightly | lightly | lightly |
| pigmentation of underside | weak | unpig-mented | lightly | unpig-mented |
| Petiolule length | short | very short | short | very short |
| Stipule orientation | erect-clasping | erect | erect-clasping | erect-clasping |
| Flowers | | | | |
| Flower color | white | white | white | white |
| Flowering period | | | | |
| primocane | mid June-mid October | mid June-early October | early June-mid Septem-ber | early June-early October |
| floricane | late March-mid June | early April-early June | early April-early June | early to mid March-early June |
| Flower size | medium | small | medium | large |
| Petal | | | | |
| length (cm) | 0.8–0.9 | 0.7–0.8 | 0.7–0.9 | 0.7–1.0 |
| width (cm) | 0.4–0.5 | 0.3 | 0.3–0.4 | 0.3–0.5 |
| Pedicel | | | | |
| coloration | present, medium inten-sity red | present, strong inten-sity red | present, strong inten-sity red | present, strong inten-sity red |
| length | medium | medium | medium | long |
| Productivity | | | | |
| Primocane | ~13.3 t/acre | ~5.1 t/acre | ~7.3 t/acre | ~6.4 t/acre |
| Floricane | ~8.1 t/acre | ~4.1 t/acre | ~2.9 t/acre | ~5.1 t/acre |

TABLE 2

FRUIT CHARACTERISTICS OF 'ANNAMARIA'

| | AnnaMaria | Heritage | Summit | Amity |
|---|---|---|---|---|
| Fruit | | | | |
| Harvest season | | | | |
| primocane | mid July to early August-November | late July-mid November | mid July-late October | mid July-mid November |
| floricane | late April-late June | mid May-mid July | mid May-mid July | late April -mid July |
| Color | Light Red | Medium Red | Medium Red | Medium Red |
| immature | 39A, 43C | 53A | 46A | 46A |
| maturing | 46D, 47A | 45A, 46D | 45A | 47A |
| mature | 45D | 44C | 42B | 42B |
| Glossiness | weak | medium | medium | medium |
| Dimensions | | | | |
| weight (g/fruit) | | | | |
| primocane | 4.0–4.5 (mean 4.2) | 2.7–2.9 (mean 2.8) | 2.5–3.3 (mean 2.8) | 2.7–3.7 (mean 3.2) |
| floricane | 3.6–4.1 (mean 3.9) | 2.3–2.7 (mean 2.6) | 2.5–2.8 (mean 2.6) | 3.0–3.4 (mean 3.2) |
| length (primocane) (mm) | 21.4–33.3 (mean 28.7) | — | 17.5–25.4 (mean 20.2) | 17.5–22.2 (mean 20.1) |
| width (primo-cane) (mm) | 20.6–27.0 (mean 23.7) | — | 18.3–23.0 (mean 20.4) | 15.9–23.0 (mean 20.2) |
| Soluble sol-ids (%) | 9.2 | — | 9.4 | 9.7 |
| Titratable acidity | | | | |
| (% as citric acid) | 11.2 | — | 14.5 | 11.2 |
| Seeds | | | | |
| weight (mg) | 1.8 | — | 1.8 | 1.5 |
| Number druplets/fruit | 103–165 (mean 142) | 45–102 (mean 72) | 73–119 (mean 98) | 62–108 (mean 88) |
| Firmness | firm | firm | firm | firm |
| Yield | very high | medium | high | medium |

TABLE 3

ISOZYME BANDING PATTERNS OF 'ANNAMARIA' COMPARED WITH 'HERITAGE' AND 'SUMMIT'

| | Isozyme and Pattern | | |
|---|---|---|---|
| Cultivar | PGI | MDH | PGM |
| AnnaMaria | A | H | C |
| Heritage | A | D | C |
| Summit | A | C | A |

We claim:

1. A new and distinctive cultivar of raspberry plant, as illustrated and described herein.

* * * * *

UNITED STATES PATENT AND TRADEMARK OFFICE

CERTIFICATE OF CORRECTION

PATENT NO. : PP11,102

DATED : October 19, 1999

INVENTOR(S) : Carlos D. Fear and Mella-Dee M. Mayberry

It is certified that error appears in the above-identified patent and that said Letters Patent is hereby corrected as shown below:

Column 1, line 4: please delete "an"

Column 1, line 44: please delete "AnnMaria" and replace with --AnnaMaria--

Column 2, line 7: please delete "followers" and replace with --followed--

Column 2, line 8: please delete "designating" and replace with --designate--

Column 2, line 19: please delete "primocare" and replace with --primocane--

Column 2, line 41: please delete "distinguishing" and replace with --distinguish--

Column 3, TABLE 1, under the heading "Primocanes", 1st entry: please insert --of-- between "number" and "fruiting"

Column 4, TABLE 1, under the heading "prickles", 2nd entry down: please delete "on" and replace with --of--

Column 4, TABLE 1, under the heading "prickles", 4th entry down: please delete "on" and replace with --of--

Column 4, TABLE 1, under the heading "prickles", 5th entry down: please delete "on" and replace with --of--

Column 4, TABLE 1, under the heading "Floricanes", 1st entry: please insert --of-- between "number" and "nodes"

Signed and Sealed this

Tenth Day of April, 2001

*Attest:*

Nicholas P. Godici

NICHOLAS P. GODICI

*Attesting Officer*

*Acting Director of the United States Patent and Trademark Office*